(12) United States Patent
Kent

(10) Patent No.: US 7,238,224 B2
(45) Date of Patent: Jul. 3, 2007

(54) FLUID-GAS SEPARATOR

(75) Inventor: Blair M Kent, Camas, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 357 days.

(21) Appl. No.: 10/977,277

(22) Filed: Oct. 29, 2004

(65) Prior Publication Data

US 2006/0090645 A1    May 4, 2006

(51) Int. Cl.
*B01D 69/00* (2006.01)
*B01D 69/04* (2006.01)
*B01D 69/06* (2006.01)

(52) U.S. Cl. ............... 95/46; 96/6; 96/7; 210/321.64; 604/126; 347/92

(58) Field of Classification Search ............ 95/46; 96/6, 7; 347/92; 604/126; 210/321.64
See application file for complete search history.

(56) References Cited

U.S. PATENT DOCUMENTS

| 4,302,223 | A | * | 11/1981 | Booth et al. .................... 96/6 |
| 4,525,182 | A | * | 6/1985 | Rising et al. .................... 96/6 |
| 4,642,098 | A | * | 2/1987 | Lundquist .................... 604/123 |
| 5,439,587 | A | * | 8/1995 | Stankowski et al. ... 210/321.64 |
| 5,659,346 | A |   | 8/1997 | Moynihan |
| 5,841,454 | A |   | 11/1998 | Hall et al. |
| 6,478,415 | B2 |   | 11/2002 | Barinaga et al. |
| 6,481,837 | B1 |   | 11/2002 | Askren et al. |
| 7,141,097 | B2 | * | 11/2006 | Leahey ..................... 96/6 |

* cited by examiner

Primary Examiner—Duane Smith
Assistant Examiner—Douglas J. Theisen

(57) ABSTRACT

A fluid-gas separator includes a gas-permeable membrane arranged sufficiently adjacent to a fluid-permeable membrane to allow the separation of fluid and gas flowing therein independent of the orientation of the fluid-gas separator itself.

22 Claims, 5 Drawing Sheets

ND-GAS SEPARATOR

BACKGROUND

Certain fluid delivery devices need to remove air or other gas from the fluid before it is delivered to a destination. By way of example, in printing devices, such as, inkjet printers, it is desirable to remove air and/or other gases from ink that is being supplied to a printhead because the printhead may malfunction when air or other gases interfere with its operation. Another exemplary fluid delivery device is an intravenous drug/fluid delivery device, wherein it is desirable to remove air or other gases prior to delivering the drug/fluid to a patient.

To remove air or other gas from a fluid, these and other like fluid delivery devices typically use a purging mechanism that separates the air/gas from the fluid. Such purging mechanisms are typically designed to operate in a particular orientation and as such may fail to operate correctly if their orientation changes. It would be desirable to have a fluid-gas separator that can operate in a variety of different orientations without failing.

BRIEF DESCRIPTION OF THE DRAWINGS

The following detailed description refers to the accompanying figures. In the figures, the left-most digit(s) of a reference number identifies the figure (Fig.) in which the reference number first appears. Moreover, the same reference numbers are used throughout the drawings to reference like features and components.

DETAILED DESCRIPTION

Figure 1:
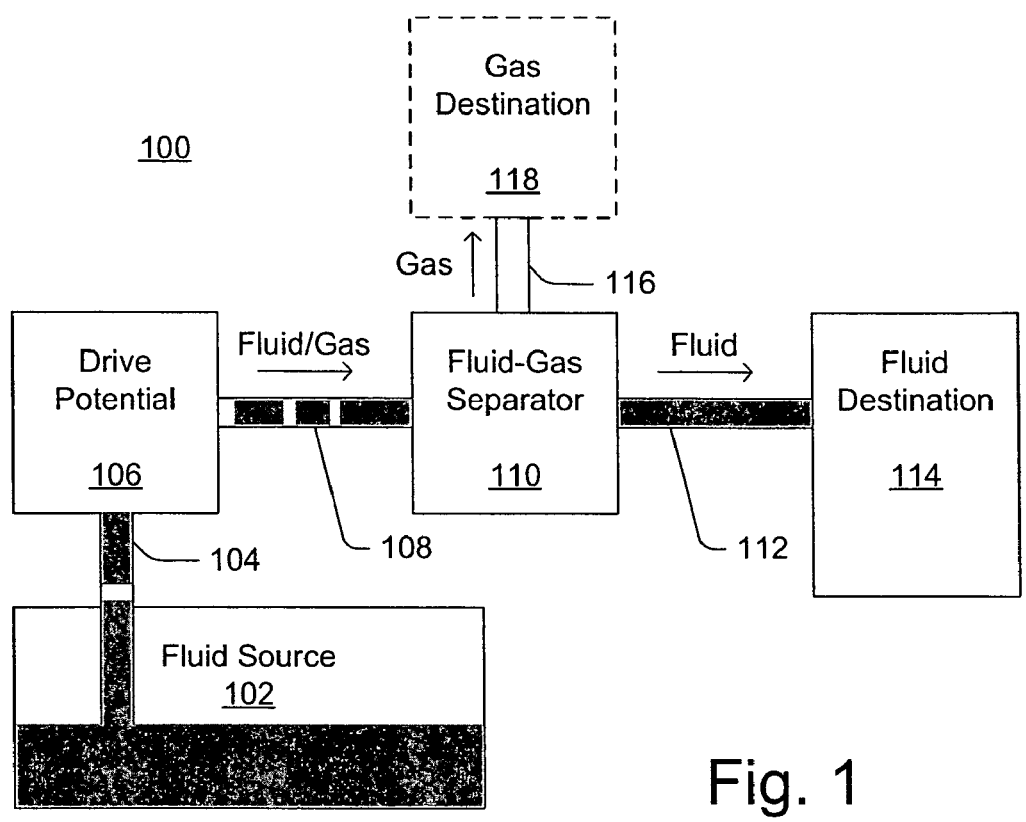
FIG. 1 is a block diagram depicting an exemplary fluid delivery device having a fluid-gas separator, in accordance with certain embodiments of the present invention.

FIG. 1 is a block diagram depicting an exemplary fluid delivery device 100, in accordance with certain embodiments of the present invention.

Fluid delivery device 100 includes a fluid source 102 that is configured to hold at least one fluid. Fluid source 102 is coupled a drive potential 106 through a conduit 104 in a manner that allows the fluid held in fluid source 102 to be withdrawn via conduit 104. Drive potential 106 is representative of a variety of mechanisms that urge the withdrawal of fluid from fluid source 102 through conduit 104 and then into conduit 108. By way of example, drive potential 106 may include a pump or the like. In certain implementations, drive potential 106 may include an arrangement that employs gravity to urge the movement of the fluid.

Conduit 108 is further coupled to an inlet of a fluid-gas separator 110. Fluid-gas separator 110 is configured to at least substantially separate gas that may be present in the urged flowing fluid. The separated gas exit fluid-gas separator 110 through a gas outlet. In this example, a conduit 116 directs the gas or gasses to an optional gas destination 118 that collects or otherwise processes the gas in some manner. In certain implementations, gas destination 118 may be configured to return the gas to fluid source 102 or into another component of device 100. In other examples, conduit 116 and/or the gas outlet may be configured to simply release the gas into the atmosphere.

Fluid-gas separator 110 also includes a fluid outlet that is coupled to conduit 112. The fluid having been separated from the gas continues to be urged by drive potential 106 through conduit 112 to at least one fluid destination 114.

Conduits 104, 108, 112, and 116 are representative of one or more structures or other arrangements that allow the urging by drive potential 106 of the fluid or fluid-gas mixture to occur. By way of example, in certain implementations such conduits may include tubes, pipes, channels, guides, filters, connectors, valves, gauges, sensors, heaters, etc.

FIG. 1 has been illustrated, through the use of gray shading, to better show the flow of fluid (shaded) and gas (non-shaded) within device 100. As shown by the breaks in the shading within conduits 104 and 108, gas may become mixed with the fluid. Fluid-gas separator 110 separates the gas from the fluid as illustrated by the continuous shading within conduit 112.

Figure 2A:
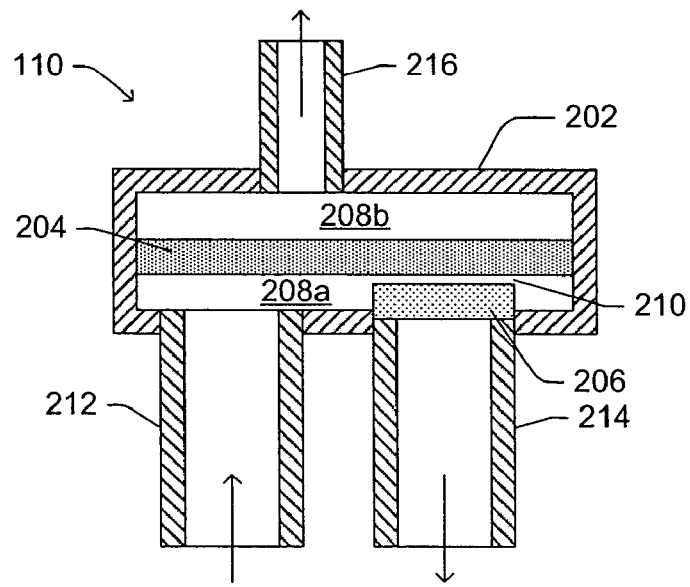
FIGS. 2A and 2B are illustrative diagrams depicting a cross-sectional view of an exemplary fluid-gas separator, in accordance with certain embodiments of the present invention.
Figure 2B:
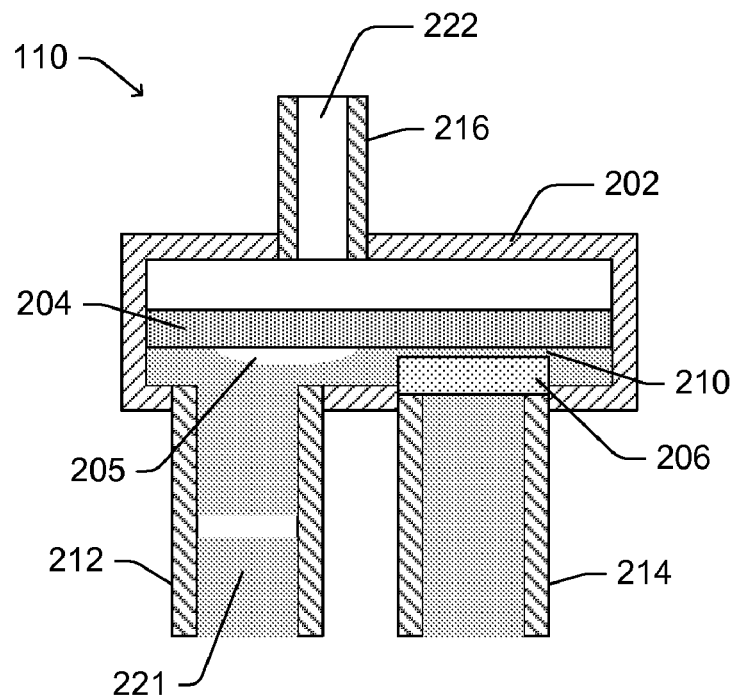

FIGS. 2A and 2B are illustrative diagrams depicting a cross-sectional view of an exemplary fluid-gas separator 110, in accordance with certain embodiments of the present invention.

As shown in FIG. 2A, fluid-gas separator 110 includes a body or housing 202 having an inlet 212 through which a fluid and gas mixture can flow into a chamber 208a within housing 202. Chamber 208a is separated by a chamber 208b by a gas-permeable membrane 204. Gas-permeable membrane 204 is configured to allow gas within chamber 208a to pass through membrane 204 and enter chamber 208b. Gas-permeable membrane 204 is configured to not allow fluid within chamber 208a to enter chamber 208b. Gas that passes through gas-permeable membrane 204 and into chamber 208b may then exit separator 110 via gas outlet 216

Figure 8:
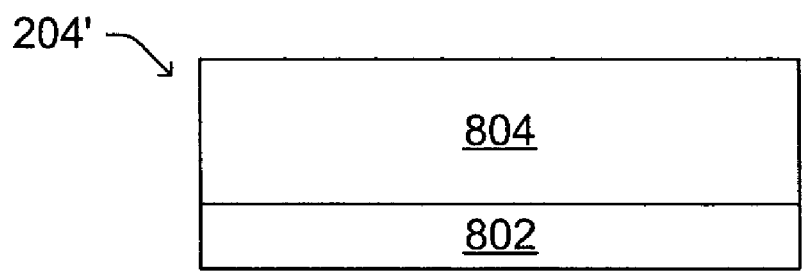
FIG. 8 is an illustrative diagram depicting a cross-sectional view of a gas-permeable membrane having a plurality of layers, in accordance with certain further embodiments of the present invention.

Gas-permeable membrane, materials are well known. Gas-permeable membrane 204 may include, for example, a hydrophobic material, an oleophobic material, or the like. As depicted in FIG. 8, gas-permeable membrane 204' may also include two or more layers of materials, such as, an interface layer 802 and a backing layer 804. Such layers may be bonded or otherwise held together. Here, interface layer 802 is configured to allow the gas to pass through it but not the fluid as described above, and backing layer 804 is configured to provide structural support to interface layer 802 while also allowing the gas to pass therethrough. Note that FIG. 8 is illustrative only and hence the layers are not necessarily drawn to scale.

Gas-permeable membrane 204/204' may include, for example, a "breathable" or microporous material such as a fabric, membrane, laminate, etc, made from polytetrafluoroethylene (PTFE), expanded PTFE, porous PTFE, or other like materials. One example, of such materials includes GORE-TEX™ ePTFE based membrane material, currently sold for packaging vents in a laminate form by W. L. Gore and Associates, Inc. of Newark, Del. This is just one example; those skilled in the art will recognize that other types of gas-permeable materials may also be used.

Fluid within chamber 208a is urged through a fluid-permeable membrane 206. Fluid-permeable membrane 206 is configured to allow fluid to pass through it from chamber 208a into a fluid outlet 214. Once properly wetted, fluid-permeable membrane 206 is configured to not allow gas to pass through it from chamber 208a into a fluid outlet 214. Instead, the gas within chamber 208a will pass through gas-permeable membrane 204 into chamber 208b as described above.

Fluid-permeable membrane 206 may include any material that exhibits appropriate fluid-permeability and gas-impermeability properties when wetted. Fluid-permeable membrane 206 may, for example, include hydrophilic, oleophilic, or other like materials. Fluid-permeable membrane 206 may include one or more materials in one or more layers. By way of example, fluid-permeable membrane 206 may include fabric, a screen, a mesh, or the like with openings sized to allow fluid to pass therethrough but not gaseous bubbles once wetted.

In accordance with certain aspects of the present invention, once gas-fluid separator 110 is properly primed with the fluid/gas mixture, the amount of pressure (e.g., bubble pressure) needed to force the gas 205 through gas-permeable membrane 204 is less than the amount of pressure needed to force the gas 205 through wetted fluid-permeable membrane 206. Conversely, while gas-fluid separator 110 is primed and operating, the amount of pressure needed to force the fluid 221 through wetted fluid-permeable membrane 206 is less than the amount of pressure needed to force the fluid 221 through non-wetted gas-permeable membrane 204.

In this example, a portion of membranes 204 and 206 are positioned adjacent one another within chamber 208a with a small gap 210 separating them. Gap 210 is small enough to prevent the gas within chamber 208a from forming one or more bubbles or a layer that significantly or completely covers fluid-permeable membrane 206. If such were to occur, then it is possible that the urged fluid may force some of the gas through fluid-permeable membrane 206. Gap 210 may be sized, therefore, based on any number of factors including, for example, the type of fluid(s), the type of gas(es), membrane characteristics, fluid pressures, etc.

Figure 7:
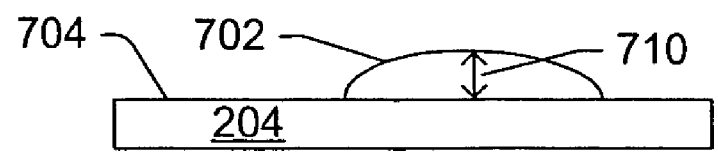
FIG. 7 is an illustrative diagram depicting a test drop height measurement technique from a side view and a top view, in accordance with certain other embodiments of the present invention.
Figure 7:
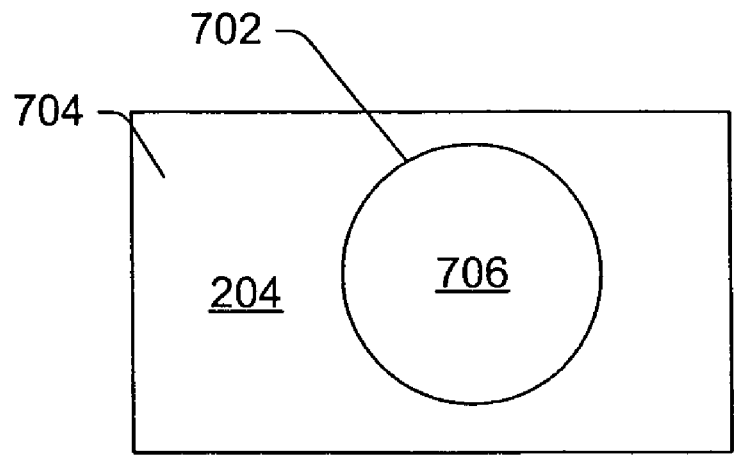

The size of gap 210 may be determined, for example, by testing gas-permeable membrane 204 using the fluid as illustrated in FIG. 7. The upper drawing shows a side view and the lower drawing shows a top view. Here, a test drop 702 of the fluid is placed onto a non-wetted surface 704 of gas-permeable membrane 204. Test drop 702, in this example, covers an area 706 that is about the same size as a corresponding area of fluid-permeable membrane 206. A test drop height 710 of test drop 702 is then measured. Test drop height 710 may then be considered to represent a maximum size (distance) for gap 210, for example, should separator 110 be intended for operations in different orientations. In certain implementations, gap 210 may therefore be sized to be less than test drop height 710.

Figure 3:
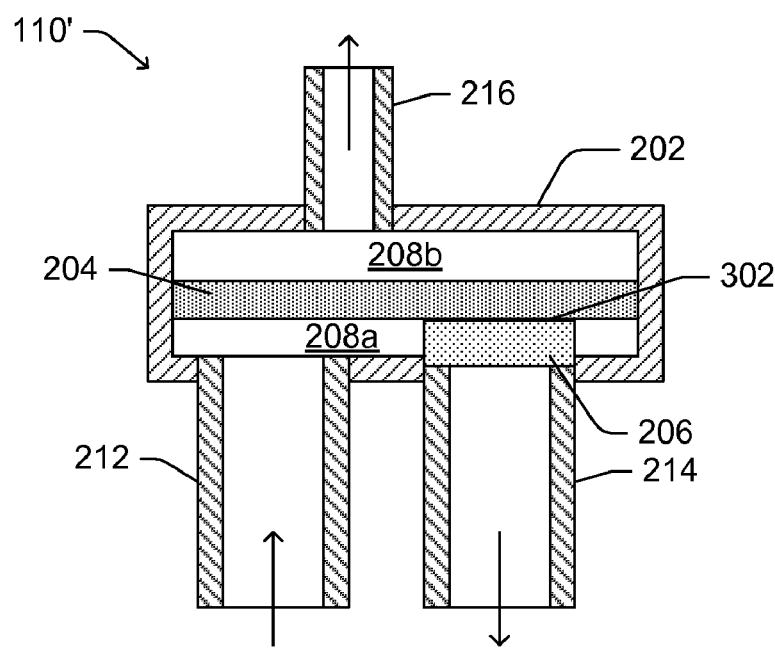
FIG. 3 is an illustrative diagram depicting a cross-sectional view of an exemplary fluid-gas separator, in accordance with certain other embodiments of the present invention.

FIG. 3 is an illustrative diagram depicting a cross-sectional view of an exemplary fluid-gas separator 110', in accordance with certain other embodiments of the present invention. Fluid-gas separator 110' is similar to fluid-gas separator 110 of FIGS. 2A-B, with the exception that gap 210 between gas-permeable membrane 204 and fluid-permeable membrane 206 no longer exists. Instead, gas-permeable membrane 204 and fluid-permeable membrane 206 are actually in physical contact with one another, forming contact interface 302. In certain embodiments, gas-permeable membrane 204 may be configured to flex or otherwise move in response to fluid pressure within chamber 208a thereby opening contact interface 302 in such a manner to allow fluid to flow from chamber 208a through fluid-permeable membrane 206.

In accordance with certain aspects of the present invention, fluidgas separators 110 and 110' can be configured to operate in multiple, it not all, orientations by selecting a small enough gap 210 or providing a contact interface 302. In such a configuration gas bubbles should come into contact with gas-permeable membrane 204 before or at about the same time that they would contact fluid-permeable membrane 206. As a result, the gas will flow through gas-permeable membrane, which is configured to provide a lower resistance for gas flow than fluid-permeable membrane 206. Thus, as pressure builds or is applied by the urging of drive potential 106 within chamber 208a the gas will be forced out of the mixture through gas-permeable membrane 204.

The exemplary embodiments of FIGS. 2A-B and FIG. 3 illustrate membranes 204 and 206 has having a substantially planer shape. It should be understood, however, that one or both of these membranes may have a non-planer shape. Furthermore, the size and/or surface area of one or more of these membranes may vary depending upon the application. Thus, in certain implementations, membrane 206 may be larger than membrane 204. Also, in certain implementations there may be more than one gas-permeable membrane, and/or more than one fluid-permeable membrane.

Figure 4:
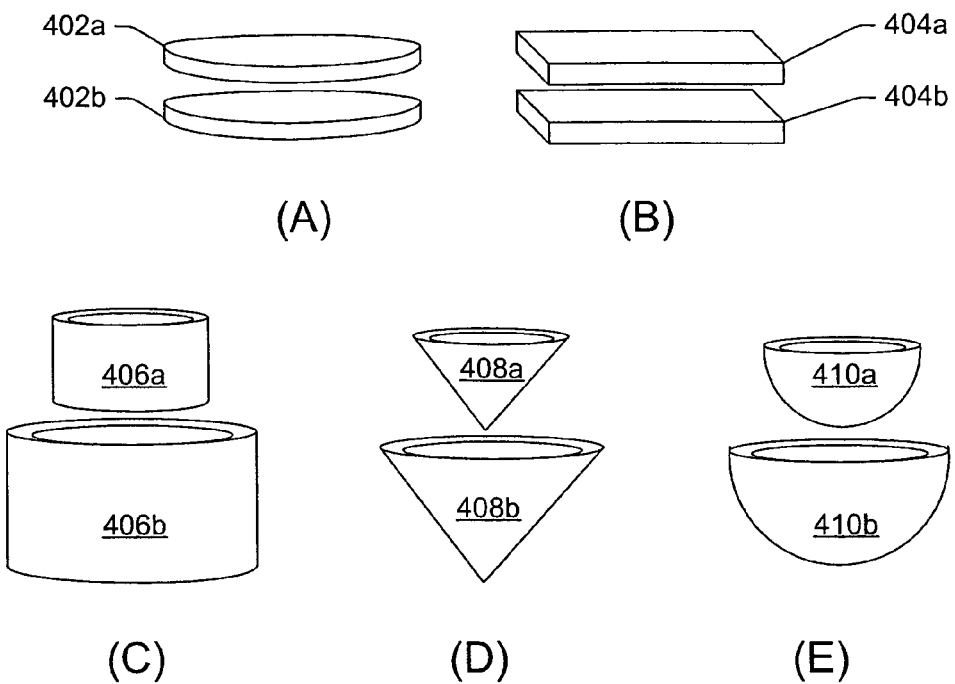
FIGS. 4A-E are illustrative diagrams depicting exemplary shapes for a gas-permeable membrane and a fluid-permeable membrane for use in a fluid-gas separator, in accordance with certain different embodiments of the present invention.

Some exemplary shapes for membranes 204 and/or 206 are illustrated in FIGS. 4A-E, in accordance with certain different embodiments of the present invention. FIG. 4A depicts a substantially planer disk shaped gas-permeable membrane 402a and a substantially planer disk shaped fluid-permeable membrane 402b. FIG. 4B depicts a substantially planer rectangular shaped gas-permeable membrane 404a and a substantially planer rectangular shaped fluid-permeable membrane 404b. FIG. 4C depicts a cylindrically shaped gas-permeable membrane 406a and a cylindrically shaped fluid-permeable membrane 406b. FIG. 4D depicts a conically shaped gas-permeable membrane 408a and a conically shaped fluid-permeable membrane 408b. FIG. 4E depicts a spherically shaped gas-permeable membrane 410a and a spherically shaped fluid-permeable membrane 410b.

Figure 5:
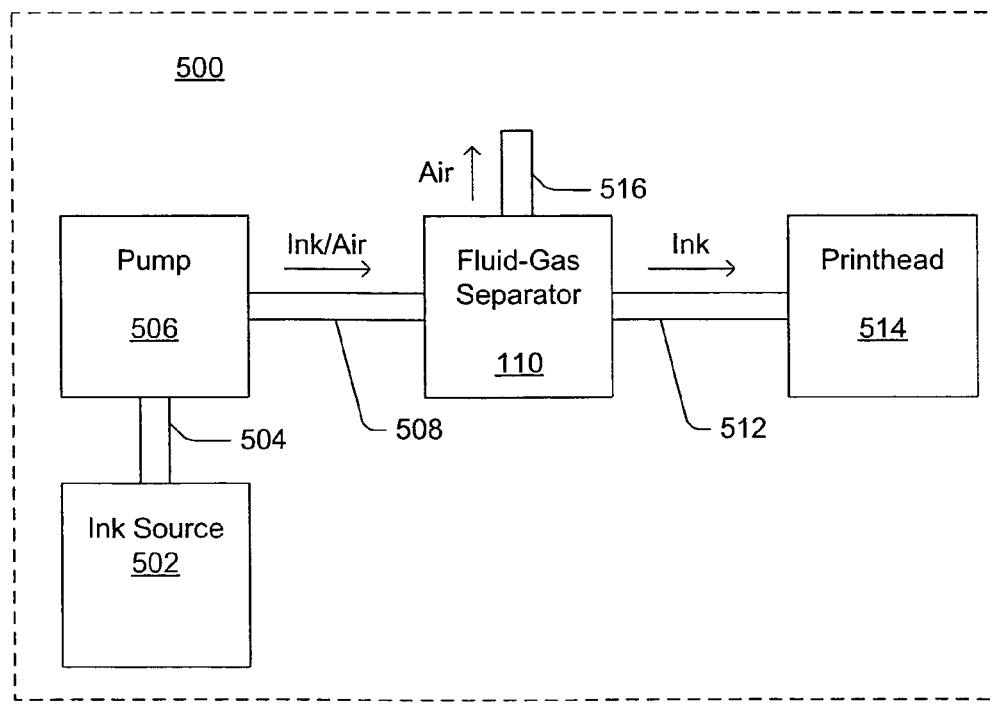
FIG. 5 is a block diagram depicting an exemplary printing device having a fluid delivery device that includes a fluid-gas separator, in accordance with certain embodiments of the present invention.

FIG. 5 is a block diagram depicting an exemplary printing device 500 having a fluid-gas separator 110 (or 110'), in accordance with certain embodiments of the present invention.

Printing device 500 includes an ink source 502 that is configured to hold ink. Ink source 502 is coupled a pump 506 through a conduit 504 in a manner that allows the ink held in ink source 502 to be withdrawn via conduit 504. Conduit 508 is further coupled to an inlet of a fluid-gas separator 110 (or 110'). Fluid-gas separator 110 (or 110') is configured to at least substantially separate air that may be present in the urged flowing ink. The separated air exits fluid-gas separator 110 (or 110') through an air outlet 516, whereby the air is released into the atmosphere.

Fluid-gas separator 110 (or 110') also includes a fluid outlet (not shown) that is coupled to conduit 512. The ink having been separated from the air continues to be urged by pump 506 through conduit 512 to a printhead 514. Printhead 514 is configured to selectively eject droplets of the ink onto a medium (not shown) as part of printing operation.

Figure 6A:
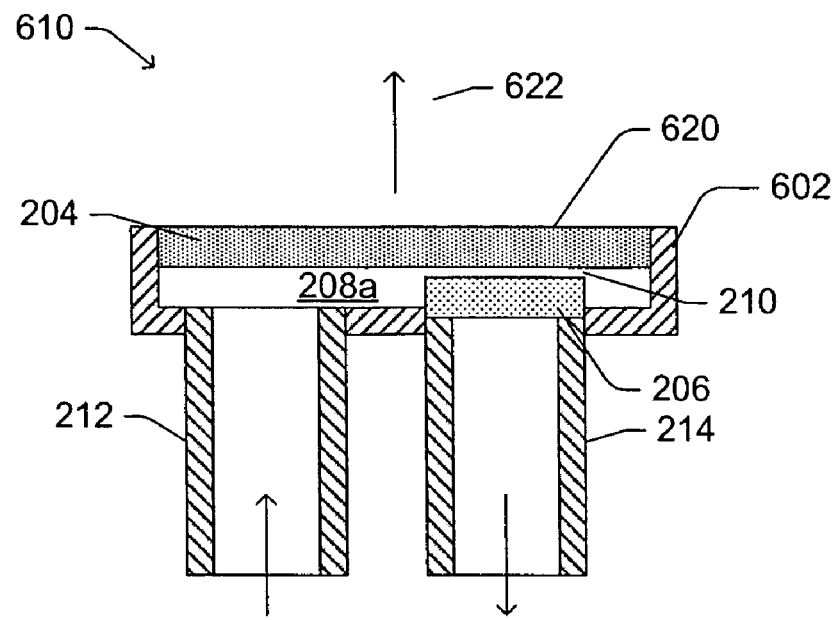
FIGS. 6A-B are illustrative diagrams depicting cross-sectional views of two exemplary fluid-gas separators, in accordance with certain other embodiments of the present invention.
Figure 6B:
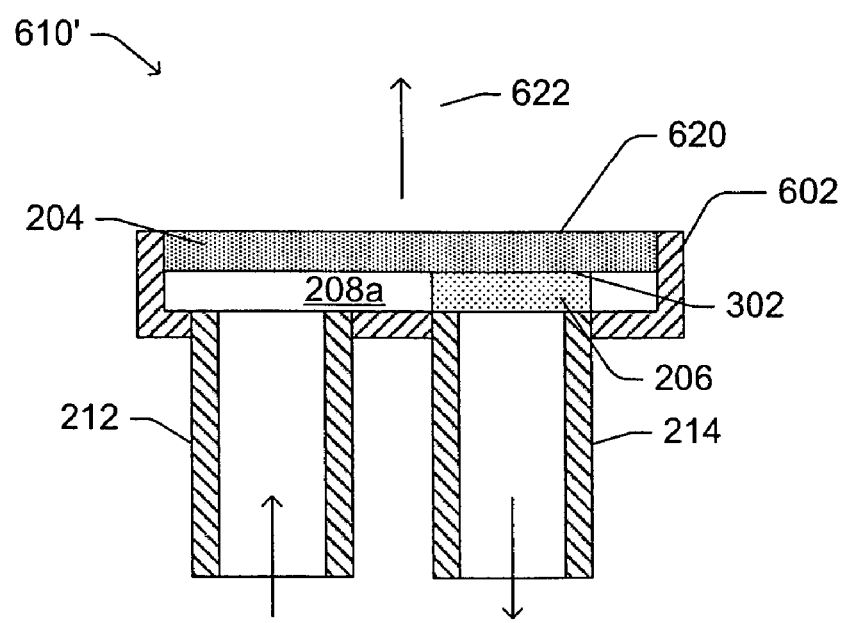

FIGS. 6A-B are illustrative diagrams depicting cross-sectional views of two exemplary fluid-gas separators 610 and 610', respectively, in accordance with certain further embodiments of the present invention. Fluid-gas separator 610 is similar to fluid-gas separator 110 and fluid-gas separator 610' is similar to fluid-gas separator 110'. In both of these examples, however, gas outlet 216 is inherently formed by housing 602 such that a back-side 620 of gas-permeable membrane 204 is directly exposed to a surrounding environment 622 which functionally serves as chamber 208b.

Although the above disclosure has been described in language specific to structural/functional features and/or methodological acts, it is to be understood that the appended claims are not limited to the specific features or acts described. Rather, the specific features and acts are exemplary forms of implementing this disclosure.

What is claimed is:

1. A fluid-gas separator comprising:
   a housing defining a chamber therein and having an inlet leading into said chamber and first and second outlets each leading out of said chamber;
   a gas-permeable membrane arranged within said housing to completely separate said chamber into a first chamber and a second chamber such that said inlet leads into said first chamber, said first outlet leads out of said first chamber and said second outlet leads out of said second chamber; and
   a fluid-permeable membrane arranged within said housing to completely cover said first outlet within said first chamber and wherein at least a portion of a surface of said fluid-permeable membrane is adjacent to at least a portion of an opposing surface of said gas-permeable membrane.

2. The fluid-gas separator as recited in claim 1, wherein said portion of said surface of said fluid-permeable membrane is separated from said portion of said opposing surface of said gas-permeable membrane by a gap less than a test drop height associated with said fluid-permeable membrane and at least one fluid.

3. The fluid-gas separator as recited in claim 1, wherein said portion of said surface of said fluid-permeable membrane contacts said portion of said opposing surface of said gas-permeable membrane.

4. The fluid-gas separator as recited in claim 1, wherein said gas-permeable membrane is configured to flex.

5. The fluid-gas separator as recited in claim 1, wherein said fluid-permeable membrane includes a metallic mesh.

6. The fluid-gas separator as recited in claim 1, wherein said gas-permeable membrane includes at least one layer comprising polytetrafluoroethylene.

7. The fluid-gas separator as recited in claim 1, wherein: said inlet is configured to direct a mixture of at least one fluid and at least one gas into said first chamber;
said first outlet is configured to direct said at least one fluid that has passed through said inlet, said first chamber and said fluid-permeable membrane out of said first chamber; and
said second outlet is configured to direct said at least one gas that has passed through said inlet, said first chamber, said gas-permeable membrane and said second chamber out of said second chamber.

8. The fluid-gas separator as recited in claim 1, wherein at least one of said fluid-permeable membrane and said gas-permeable membrane have at least a part of at least one surface in a shape selected from a group of shapes comprising an at least substantially planer shape, a non-planer shape, a curved shape, a disk shape, a rectangular shape, a cylindrical shape, a conical shape, and a spherical shape.

9. The fluid-gas separator as recited in claim 1, wherein said gas-permeable membrane includes at least one membrane selected from group of membranes comprising a hydrophobic membrane and an oleophobic membrane.

10. The fluid-gas separator as recited in claim 1, wherein said fluid-permeable membrane includes at least one membrane selected from group of membranes comprising a hydrophilic membrane and an oleophilic membrane.

11. A fluid-gas separator comprising:
    a gas-permeable membrane establishing a boundary between a fluid-side chamber and a gas-side region, wherein said gas-side region is inside a gas-side chamber;
    an inlet configured to direct a flow of materials into said fluid-side chamber, wherein said flow of materials includes at least one fluid and at least one gas;
    a fluid outlet having a fluid-permeable membrane cover, said fluid outlet configured to direct said at least one fluid out of said fluid-side chamber through said fluid-permeable membrane cover;
    a gas outlet directing said at least one gas out of said gas-side chamber after passing through said gas-permeable membrane; and
    wherein a surface of said fluid-permeable membrane cover is positioned adjacent to an opposing surface of said gas-permeable membrane.

12. The fluid-gas separator as recited in claim 11, wherein at least one of said fluid-permeable membrane cover and said gas-permeable membrane have at least a portion of at least one surface in a shape selected from a group of shapes comprising an at least substantially planer shape, a non-planer shape, a curved shape, a disk shape, a rectangular shape, a cylindrical shape, a conical shape, and a spherical shape.

13. A fluid-gas separator comprising:
    a gas-permeable membrane establishing a boundary between a fluid-side chamber and a gas-side region;
    an inlet configured to direct a flow of materials into said fluid-side chamber, wherein said flow of materials includes at least one fluid and at least one gas;
    a fluid outlet having a fluid-permeable membrane cover, said fluid outlet configured to direct said at least one fluid out of said fluid-side chamber through said fluid-permeable membrane cover; and
    wherein a surface of said fluid-permeable membrane cover contacts an opposing surface of said gas-permeable membrane.

14. The fluid-gas separator as recited in claim 13, wherein said gas-side region is inside a gas-side chamber and further comprising:

a gas outlet directing said at least one gas out of said gas-side chamber after passing through said gas-permeable membrane.

15. The fluid-gas separator as recited in claim 13, wherein at least one of said fluid-permeable membrane cover and said gas-permeable membrane have at least a portion of at least one surface in a shape selected from a group of shapes comprising an at least substantially planer shape, a non-planer shape, a curved shape, a disk shape, a rectangular shape, a cylindrical shape, a conical shape, and a spherical shape.

16. The material delivery device comprising:

a drive configured to output a flow of materials including at least one fluid and at least one gas; and a separator coupled to receive said flow of materials, said separator including a gas-permeable membrane dividing a chamber into a fluid-side chamber and a gas-side chamber, an inlet directing said flow of materials into said fluid-side chamber, a fluid outlet covered by a fluid-permeable membrane directing said at least one fluid out of said fluid-side chamber after passing through said fluid-permeable membrane, a gas outlet directing said at least one gas out of said gas-side chamber after passing through said gas-permeable membrane, and wherein a surface of said fluid-permeable membrane is positioned adjacent to an opposing surface of said gas-permeable membrane.

17. The material delivery device as recited in claim 16, further comprising:

a source coupled to said drive, said source being configured to provide said at least one fluid to said drive.

18. The material delivery device as recited in claim 16, further comprising:

a destination coupled to receive said at least one fluid from said fluid outlet.

19. The material delivery device as recited in claim 16, further comprising:

a destination coupled to receive said at least one gas from said gas outlet.

20. A method comprising:

receiving a flow of materials including at least one fluid and at least one gas;

causing said flow of materials to contact a gas-permeable membrane through which said at least one gas passes through but said at least one fluid does not pass through; and causing said flow of materials to contact a fluid-permeable membrane through which said at least one fluid passes through but said at least one gas does not pass through, and wherein a surface of said fluid-permeable membrane contacts an opposing surface of said gas-permeable membrane.

21. A printing device comprising:

a pump configured to output a flow of materials including ink and at least one gas; and a fluid-gas separator coupled to receive said flow of materials, said fluid-gas separator including a gas-permeable membrane dividing a chamber into a fluid-side chamber and a gas-side chamber, an inlet directing said flow of materials into said fluid-side chamber, a fluid outlet covered by a fluid-permeable membrane directing said ink out of said fluid-side chamber after passing through said fluid-permeable membrane, a gas outlet directing said at least one gas out of said gas-side chamber after passing through said gas-permeable membrane, and wherein a surface of said fluid-permeable membrane is positioned adjacent to an opposing surface of said gas-permeable membrane.

22. The printing device as recited in claim 21, further comprising:

an ink source configured to supply said ink to said pump; and a printhead coupled to receive said ink from said fluid outlet of said fluid-gas separator.

* * * * *